United States Patent [19]

Banks

[11] Patent Number: 5,086,178

[45] Date of Patent: Feb. 4, 1992

[54] FLUORINATED DIAZABICYCLOALKANE DERIVATIVES

[75] Inventor: Ronald E. Banks, Stockport, England

[73] Assignee: Air Products and Chemicals, Inc., Allentown, Pa.

[21] Appl. No.: 585,765

[22] Filed: Sep. 20, 1990

[51] Int. Cl.$^5$ ............... C07D 487/08; C07D 519/00; C07B 39/00

[52] U.S. Cl. ................... 544/351; 540/472; 540/556; 568/775; 568/364; 568/656; 570/261; 570/123

[58] Field of Search .............. 544/351; 540/472, 556

[56] References Cited

U.S. PATENT DOCUMENTS 4,479,901 10/1984 Barnette .................... 260/239
4,828,764  5/1989 DesMarteau ............. 260/397.45

FOREIGN PATENT DOCUMENTS 3623184 1/1988 Fed. Rep. of Germany .

OTHER PUBLICATIONS

Banks, Chem. Abs. 106, 175398v (1986).
R. E. Banks, et al, "Fluorination of 2-Nitropropane and Malonic Ester with Undecafluoropiperidine", Chem. and Ind., (1964), p. 1864.
R. E. Banks, et al, "N-Fluoro Compounds, Port IV Photochemical and Fluoride-initiated Reactions between Perfluoro-N-Fluoropiperidine and Perfluoropropene" (J. Chem. Soc., Perkin Transactions I, (1972), p. 1098.
R. L. Banks, et al, "N-Halogeno Compounds, Part 9, N-Fluoroquinolidinium Fluoroide-A New Electrophilic Fluorinating Agent", J. Chem. Soc., Perkins Trans. I, (1988), pp. 2805.
R. L. Banks, "Polymeric Analogues of Electrophilic Fluorinating Agents of the NF Class", J. Fluorine Chem., (1986), 34, p. 281.
S. T. Purrington et al., "1-Fluoro-2-pyridone: A Useful Fluorination Reagent", & Ang. Chem., (1983), 48, p 761.
S. T. Purrington et al., "Selective Fluorinations with 1-Fluoro-2-Pyridone", J. Fluorine Chem., (1984), p. 43.
E. Differding, et al, "New Fluorinating Reagents, I. The First Enantioselective Fluorination Reaction", Tetrahedron Lett., (1981), 29, p. 6087.
R. L Banks et al, "N-Halogeno-Compounds, Part 10, N-Fluoroquinuolidinium Triflate" J. Fluorine Chemistry, (1988), 41, p. 297.
I. V. Vigalak, et al., "Salts of Organic Fluoronitrogen 1-Fluoro-1-Alkyl-2,2,6,6-Tetramethylpiperidinuium Cation", J. Org. Chem., USSR, (1983) 19, pp.1203.
T. Uemoto et al. "N-Fluoropyridinium Triflate and its Analogs, The First Stable 1;1 Salts of Pyridine Nucleus and Halogen Atom", Tetrahedron Letts., vol. 27, (1986), pp. 3271.
T. Umemoto et al., "N-Fluoropyridinium Triflate and its Derivatives; Useful Fluorinating Agents", Tetrahderon Letters, vol. 27, (1986), p. 4465.
T. Umemto et al, "$\alpha$-Fluorination of Sulfides with N-Fluoropyridinium Triflates", Bull. Chem. Soc. Jpn., (1986), vol. 59, p. 3625.
S. T. Purrington et al, "The Application of Elemental Fluorine in Organic Synthesis", Chem. Rev., 1986, 86, p. 997.
G. G. Furin, "Some Electrophilic Fluorination Agents", Eds. L. Arman and S. Zanskov, Springer-Verlag Berlin, 1989, pp. 35-68.

*Primary Examiner*—Mark L. Berch
*Attorney, Agent, or Firm*—Mark L. Rodgers; William F. Marsh; James C. Simmons

[57] ABSTRACT

Fluorinated diazabicycloalkane derivative of the following Formula I:

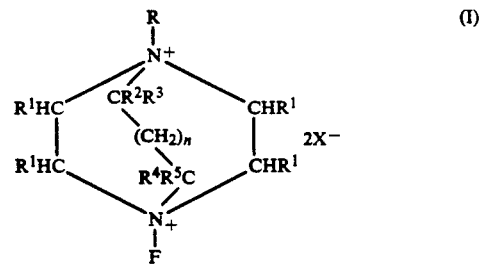

wherein n represents 0, 1 or 2; R represents a quaternizing organic group; each $R^1$, $R^2$, $R^3$, $R^4$ and $R^5$ independently represents hydrogen, $C_1$-$C_6$ alkyl, aryl, $C_1$-$C_6$ alkyl-substituted aryl or aryl-substituted $C_1$-$C_6$ alkyl and each $X^-$ independently represents a conterion or $2X^-$ represents a single divalent counterion, are electrophilic fluorinating agents.

19 Claims, No Drawings

FLUORINATED DIAZABICYCLOALKANE DERIVATIVES

TECHNICAL FIELD OF THE INVENTION

The present invention relates to electrophilic fluorinating agents of the N-F class and provides novel fluorinated diazabicycloalkane derivatives, methods for their preparation, and their use as fluorinating agents.

BACKGROUND OF THE INVENTION

There is a demand for fluorinating agents which are site-selective towards organic, especially carbanionic, substrates, especially for use in the preparation of pharmacologically active compounds. A number of such electrophilic fluorinating agents are known but are limited in their commercial utility in that they are expensive, hazardous, inconvenient to handle, lack stability and/or are insufficiently selective for general use.

Fluorine ($F_2$) solutions in halogenated or other suitable solvents at low temperature (about $-78°$ C.), trifluoromethyl hypofluorite ($CF_3OF$), caesium fluorosulphate ($CsSO_4F$) and perchloryl fluoride ($FClO_3$) are all active electrophilic fluorinating agents (S. T. Purrington, et al., Chem. Rev., 1986, 86, 997 and G. G. Furin in "New Fluorinating Agents in Organic Synthesis", Ed. L. German and S. Zemskov, Springer-Verlag: Berlin, 1989, 35–68) but are either not sufficiently selective or too hazardous for general use. Xenon difluoride ($XeF_2$) is potentially less hazardous but is too expensive in many applications.

Recently attention has been directed to the use of compounds of the N-F class, i.e. having an N-F bond, as electrophilic fluorinating agents. The prototypical member of this class is perfluoro-N-fluoropiperidine (R. E. Banks and G. E. Williamson, Chem. Ind. (London), 1964, 1864 and R. E. Banks et al, J. Chem. Soc., Perkin Trans. I, 1972, 1098). However, this compound is obtainable only in low yields by electrochemical fluorination of pyridine (about 8% yield) or 2-fluoropyridine (about 13% yield) in anhydrous hydrogen fluoride. Further, it has been found to be inadequately reactive in several applications and, on transfer of fluorine to a carbanionic substrate, liberates the imidoyl fluoride perfluoro-1-azacyclohex-1-ene which then competes for the substrate. Similar problems militate against use of the analogous compounds perfluoro-(N-fluoro-2,6-dimethylpiperidine) and perfluoro-N-fluoromorpholine (R. E. Banks et al, J. Chem. Soc., Perkin Trans. I, 1988, 2805) and of poly[perfluoro-(N-fluoropiperidin-4-ylethylene)] (R. E. Banks & E. Tsiliopoulos, J. Fluorine Chem., 1986, 34, 281) as electrophilic fluorinating agents.

Other members of the N-F class include N-fluoropyridin-2(1H)-one (S. T. Purrington and W. A. Jones, J. Org. Chem. 1983, 48, 761 and J. Fluorine Chem., 1984, 26, 43), N-fluoro-N-sulfonamides (U.S. Pat. Nos. 4479901, 4828764 and DE 3623184A) and N-fluoro-sultams (E. Differding and R. W. Lang, Tetrahedron Lett., 1988, 29, 6087).

More recently, interest in N-F class fluorinating agents has centered on N-fluoro quaternary nitrogen heterocyclic compounds, specifically N-fluoroquinuclidinium salts (R. E. Banks et al, J. Chem. Soc., Perkin Trans I, 1988, 2805 and R. E. Banks & I. Sharif, J. Fluorine Chem., 1988, 41, 297), N-fluoro-N-alkyl-2,2,6,6-tetramethylpiperidinium chlorate (I. V. Vigalok et al, J. Org. Chem. USSR, 1983, 19, 1203), and N-fluoropyridinium salts (Umemoto et al, Tetrahedron Lett., 1986, 27, 3271 & 4465 and T. Umemoto & G. Tomizawa, Bull. Chem. Soc. Jpn, 1986, 59, 3625).

The most attractive of these new fluorinating agents are the N-fluoropyridinium and, especially, N-fluoroquinuclidinium triflates (i.e. trifluoromethanesulfonates). Although pyridine is relatively cheap and readily available, quinuclidine is relatively expensive and in short supply. Further, because the hydrogen atoms at the 2 and 6 positions of N-fluoropyridinium compounds are quite acidic, difficulties arise when using the compounds with certain highly basic substrates (see T. Umemoto and G. Tomizawa, J. Org. Chem., 1989, 54, 1726).

SUMMARY OF THE INVENTION

It is an object of the present invention to provide effective electrophilic fluorinating agents which are stable and relatively inexpensive. It is a further object to provide such agents which are readily obtainable from starting materials which are presently commercially available in substantial quantities. As explained in further detail below, it has been found that novel N-fluorinated 1,4-diazabicyclo[2,2,2]octane derivatives fulfill these requirements.

DETAILED DESCRIPTION OF THE INVENTION 1,4-Diazabicyclo[2,2,2]octane (otherwise tetraethylenediamine, TEDA) is commercially available under, for example, the Trade Mark DABCO (Air Products and Chemicals, Inc.) for use in the manufacture of urethane foams, elastomers and coatings, epoxy resins, and the like articles. N,N-Tetrahalo-1,4-diazabicyclo[2,2,2]-octanes in which the halogen is chlorine, bromine or iodine are known and can readily be prepared from TEDA by, for example, treatment with the halogen in carbon tetrachloride (see U.S. Pat. No. 2964526). However, the corresponding tetrafluoro compound is unknown and cannot be prepared in an analogous manner.

Attempts to fluorinate TEDA with fluorine to produce 1,4-difluoro-1,4-diazoniabicyclo[2,2,2]octane difluoride gave an unidentified white solid which showed some fluorinating capacity but readily decomposed at ambient temperature into a coloured material having no electrophilic fluorinating power.

It has now surprisingly been found that if one nitrogen atom of TEDA is quaternized, the resultant product can readily be fluorinated at the unquaternized nitrogen atom to provide a stable, effective electrophilic fluorinating agent. Other 1,4-diazabicycloalkanes can similarly be mono-quaternized and subsequently fluorinated.

According to a first aspect of the present invention, there is provided novel N-fluorinated diazabicycloalkane derivatives of the following Formula I

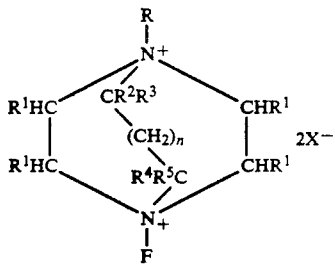

wherein n represents 0, 1 or 2; R represents a quaternizing organic group; each $R^1$, $R^2$, $R^3$, $R^4$ and $R^5$ independently represents hydrogen, $C_1$-$C_6$ alkyl, aryl, $C_1$-$C_6$ alkyl-substituted aryl or aryl-substituted $C_1$-$C_6$ alkyl. and each $X^-$ independently represents a counterion or $2X^-$ represents a single divalent counterion.

The group R can be any group which will quaternize one nitrogen atom of a diazabicycloalkane and is inert to the subsequent fluorination of the other nitrogen atom thereof in the sense that it does not prevent said fluorination. Suitable quaternizing groups include alkyl, optionally substituted by aryl and/or electron-withdrawing groups.

Alkyl groups represented by R can have 1 to 16, usually 1 to 8, especially 1 to 4, carbon atoms. Said alkyl groups can be substituted by aryl (including aromatic heterocyclic groups), especially phenyl and, additionally or alternatively, by one or more electron-withdrawing groups, especially halogen, particularly fluorine, or 1-azonia-azabicycloalkane, optionally quaternized at the second nitrogen atom by, for example, fluorine, particularly 4-fluoro-1,4-diazoniabicyclo[2,2,2]-octane (ie.

Presently, the preferred groups represented by R are:
  (a) aliphatic unsubstituted linear or branched $C_1$-$C_{16}$ alkyl, especially $C_1$-$C_4$ alkyl, particularly methyl or ethyl;
  (b) benzyl optionally substituted by up to three $C_1$-$C_4$ alkyl groups;
  (c) $C_1$-$C_{10}$ perfluoroalkyl, for example trifluoromethyl and perfluoro-octyl;
  (d) $C_1$-$C_{16}$ partially halogenated alkyl, for example 2,2,2-trifluoroethyl or chloromethyl; and
  (e) 3-(4-fluoro-1,4-diazoniabicyclo[2,2,2]oct-1-yl)-propyl (ie.

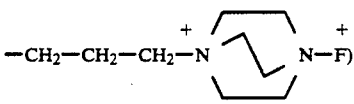

When any of $R^1$ to $R^5$ is other than hydrogen, it is preferably benzyl, phenyl or, especially, $C_1$-$C_4$ alkyl, particularly methyl. It will be understood that due to steric considerations it is not possible to obtain compounds of Formula I with all possible combinations of $R^1$ to $R^5$ values.

Usually no more than one $R^1$ at the 2 and 3 ring positions and no more than one $R^1$ at the 5 and 6 ring positions will be other than hydrogen. It is presently preferred that all $R^1$ are hydrogen.

Usually no more than one of $R^2$, $R^3$, $R^4$ and $R^5$ is other than hydrogen. Presently it is preferred that all of $R^2$ to $R^5$ are hydrogen.

The counterion(s) represented by $2X^-$ can be any anion(s) which can be counterion(s) to the quaternizing group R. Usually, not necessarily, the counterions will be weakly-nucleophilic. Suitable anions include halides, especially fluoride ($F^-$); fluorosulfate ($SO_3F^-$); alkanesulfonates, especially methanesulfonate ($CH_3SO_3^-$); alkyl sulfates, especially methyl sulphate ($CH_3SO_4^-$); perfluoroalkanesulfonates, preferably triflate ($CF_3SO_3^-$) and nonaflate ($C_4F_9SO_3^-$); arenesulfonates, especially tosylate (ie. p-toluenesulfonate; $CH_3C_6H_4SO_3^-$); alkanecarboxylates; perfluoroalkanecarboxylates; tetrafluoroborate ($BF_4^-$); tetraphenylborate ($Ph_4B^-$); hexafluorophosphate ($PF_6^-$); hexafluoroantimonate ($SbF_6^-$); chlorate ($ClO_3^-$); and sulfate ($SO_4^{--}=2X^-$). Presently preferred anions are fluoride, tetrafluoroborate, triflate and tosylate and it is presently particularly preferred that one $X^-$ is tosylate or triflate and the other $X^-$ is triflate.

It is preferred that n is 0, and each $R_1$ is hydrogen (ie. that the compounds of Formula I are derivatives of TEDA). Thus, according to a preferred embodiment, the invention provides novel N-fluorinated 1,4-diazabicyclo[2,2,2]octane derivatives of the following Formula II

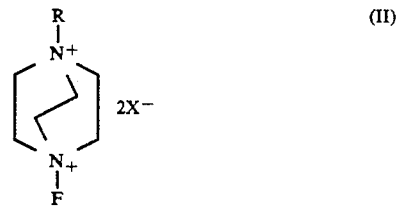

wherein R and $X^-$ are as defined above.

The compounds of Formula I can be prepared by fluorinating the corresponding N-substituted diazabicycloalkane derivative of the following Formula III

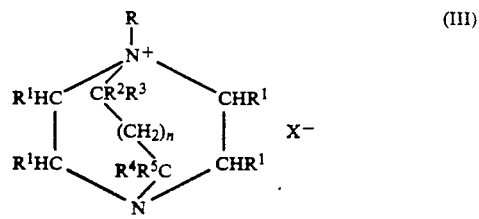

wherein n, R, $R^1$ to $R^5$, and $X^-$ are as defined above.

Suitably, the fluorination is carried out in manner known per se using a stirred-tank batch reactor into which the fluorine is admitted either as a single charge of the gas at sub-atmospheric pressure or as a continuous flow of fluorine blended with nitrogen or other inert diluent at about atmospheric pressure. In the first of said fluorination methods, fluorine is passed into a stirred low temperature solution or suspension of the N-substituted diazabicycloalkane reactant (III) in a suitable organic solvent, especially trichlorofluoromethane or acetonitrile (see R. E. Banks et al, J. Chem. Soc., Perkin Trans. I, 1988, 2805 and R. E. Banks & I. Sharif, J. Fluorine Chem., 1988, 41, 297). Usually, the temperature is in the range −35° C. to −78° C. and the fluorine pressure is below about 20 mmHg (2.7 kPa). In the second method, fluorine heavily diluted with an inert gas, usually nitrogen, is passed through said solution at about ambient pressure (see U.S. Pat. No. 4479901). In both cases, an additive such as lithium triflate or tosylate may be added to provide a counterion to replace the fluoride formed.

At least some of the N-substituted diazabicycloalkane derivatives (III) are known compounds. They can be prepared in a manner known per se by treatment of the parent diazabicycloalkane derivative of the following Formula IV with a compound of the following Formula V in a suitable organic solvent (see, for example, K. Imamura et al, Bull. Chem. Soc. Jpn. 1986, 59, 2699).

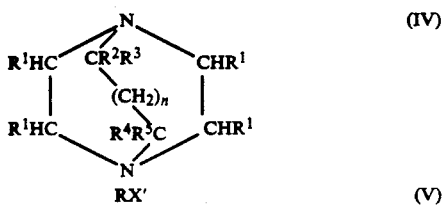

(IV)

RX'  (V)

wherein n and $R^1$ to $R^5$ are as defined above and X' is a nucleofugal group within the definition of X above or a nucleofugal group which can be exchanged for a non-nucleofugal group within said definition of X.

Presently preferred solvents include dichloromethane, acetonitrile and light petroleum ether.

Although X⁻ (or X') in Formulae I, II and III preferably is triflate, some triflates such as methyl triflate are toxic and hence it is preferred to use the corresponding tosylate and then subsequently replace tosylate with triflate in manner known per se, for example by treatment of the tosylate of Formula III with lithium triflate. More generally, counterions in the compounds of Formula III can be replaced, if required, by other counterions in manner known per se.

The compounds of Formula IV are known per se or can be prepared by analogous methods to those known per se. In particular, those compounds of Formula IV in which n is 0 can be obtained by acid-catalyzed ring closure of the corresponding N-(hydroxyethyl) piperazine. Those N-(hydroxyethyl) piperazines can be obtained by reaction of the corresponding piperazine with ethylene oxide or an appropriately substituted ethylene oxide. Substituted piperazine reactants can be obtained by reaction of an ethanolamine, an ethylene oxide and ammonia with the ethanolamine and/or ethylene oxide being appropriately substituted. The diazaoicyclononane derivatives in which n is 1 or 2 can be obtained by treatment of the corresponding piperazine or homopiperazine with an appropriate alkyldihalide.

The novel fluorinating agents of Formula I are used in manner know per se as electrophilic fluorinating agents (see, for example, R. E. Banks et al J. Chem. Soc. Perkin Trans. I, 1988, 2805).

The invention is illustrated by the following non-limiting Examples.

EXAMPLE 1

1-Fluoro-4-methyl-1,4-diazoniabicyclo[2,2,2]octane Ditriflate (A) 1-Methyl-4-aza-1-azoniabicyclo[2,2,2]octane Tosylate and 1,4-Dimethyl,H-diazonia-bicyclo[2,2,2]octane Ditosylate 1

Methyl tosylate (methyl p-toluenesulfonate; 26 g, 140 mmol) dissolved in AnalaR (TM) dichloromethane (25 cm³) was added slowly (60 min.) to a cold (0° C.) magnetically stirred solution of 1,4-diazabicyclo[2,2,2]octane (15.7 g, 140 mmol) in AnalaR dichloromethane (50 cm³) under an atmosphere of dry nitrogen in a three-necked flasked fitted with a dropping funnel and double-surface water-cooled condenser equipped with a drying tube (CaCl₂). The mixture was stirred overnight at room temperature and then filtered to remove crude 1,4-dimethyl-1,4-diazoniabicyclo[2,2,2]octane ditosylate (4.2 g) contaminated with about 25 mol % of 1-methyl-4-aza-1-azoniabicyclo[2,2,2]octane tosylate (¹H n.m.r. analysis). Recrystallization of the mixture from ethanol gave a pure sample of said ditosylate (Found: C, 54.6; H, 6.9; N, 5.9; S, 13.0%. Calc. C, 54.5; H, 6.6; N, 5.8; S, 13.2%) δH(220 MHz; soln. in D₂O, ext. TMS ref.) 2.36 (s; 4-CH₃C₆H₄SO₃−), 3.34 (s; 2×CH₃N+), 4.01 (s; 6×CH₂), 7.53 (center of AB-system (d, 7.36; d, 7.70); C₆H₄) p.p.m. [residual H in D₂O, 4.78(s) p.p.m.]. Rotary evaporation of the filtrate under reduced pressure gave 1-methyl-4-aza-1-azoniabicyclo[2,2,2]octane tosylate (34.0 g, 114 mmol, 81.5%), m.p. 139°–141° C. (the sample discolored at 135° C.), shown by ¹H n.m.r. analysis to contain a trace of said ditosylate. The monotosylate was purified by shaking the sample with hot tetrahydrofuran (THF) removing the insoluble ditosylate by filtration and then evaporating the THF solution to give the pure monotosylate as a white hygroscopic solid (Found C,56.0; H, 7.7; N, 9.5; S, 10.3%. Calc. C, 56.4; H, 7.4; N, 9.4; S, 10.7%), m.p. 141°–142 ° C., δH (220 MHz; soln. in D₂O; ext. TMS ref.) 2.34 (s; 4-CH₃C₆H₄SO₃), 2.95 (s; CH₃N+), 3.08 (m; 3×CH₂), 3.28 (m; 3×CH₂), 7.52 (center of AB-system (d, 7.35; d, 7.69); C₆H₄) p.p.m. [residual H in D₂O, 4.77 (s) p.p.m.].

(B) Conversion of 1-Methyl-4-aza-1-azoniabicyclo[2,2,2]octane Tosylate to the corresponding Triflate Lithium triflate (9.54 g, 61.2 mmol) in acetonitrile (40 cm³) was added dropwise to a stirred solution of 1-methyl-4-aza-1-azoniabicyclo[2,2,2]octane tosylate (18.23 g, 61.2 mmol) in acetonitrile (125 cm³) under an atmosphere of dry nitrogen at room temperature and the mixture left stirring overnight. A white precipitate which had formed was recovered by filtration and washed with dry acetonitrile. Rotary evaporation of the combined filtrate and washings under reduced pressure gave slightly impure (by nmr analysis) 1-methyl-4-aza-1-azoniabicyclo[2,2,2]octane triflate (11.92 g). Continuous extraction (Soxhlet) of the precipitate with dry acetonitrile, followed by evaporation of the extraction solution gave a further 3.34 g of said triflate (total yield 15.26 g, 55.3 mmol, 90%). Lithium tosylate (10.0g, 56.2 mmol, 91.5%) was recovered from the thimble. 1-Methyl-4-aza-1-azoniabicyclo [2,2,2]octane triflate was recrystallised from ethanol-diethyl ether to give analytically pure material (Found: C, 34.9; H, 5.6; F, 20.6; N, 9.8%. Calc. C, 34.8; H, 5.4; F. 20.6; N, 10.1%), m.p.

214°–217° C. (dec ), δH (200 MHz; D$_2$O soln., ext. TMS ref) 3.05 (s; CH$_3$N$^+$), 3.20 (m; 3×CH$_2$), 3.38(m; 3×CH$_2$) p.p.m. [residual H in D$_2$O, 4.73 (s) p.p.m.], δF (same soln.; ext. CF$_3$CO$_2$H ref.) 0.5 p.p.m. (s; CF$_3$SO$_3^-$).

(C) Direct production of 1-Methyl-4-aza-1-azoniabicyclo[2,2,2]octane Triflate Methyl triflate (methyl trifluoromethanesulfonate) (8.7 g, 52.6 mmol) was added dropwise during 60 minutes to a cold (0° C.) magnetically stirred solution of 1,4-diazabicyclo[2,2,2]octane (5.9 g, 52.9 mmol) in acetonitrile (50 cm$^3$) under an atmosphere of dry nitrogen. The mixture was stirred overnight at room temperature and then filtered to remove a white solid product. Recrystallization of this material from methanol gave 1,4-dimethyl-1,4-diazoniabicyclo[2,2,2]-octane ditriflate (6.0 g, 13.6 mmol, 52%) (Found: C, 27,2; H, 4.0; F, 25.0; N, 6.2%. Calc. C, 27.3; H, 4.1; F, 25.9; N, 6.4%), m.p. 278°–280° C. (dec.), δH (D$_2$O soln., ext. TMS ref) 3.50 (s; 2×CH$_3$N$^+$), 4.16 (s; 6×CH$_2$) p.p.m. [residual H in D$_2$O, 4.90 p.p.m.]. The white solid residue obtained by rotary evaporation of the filtrate was recrystallized from ethanol to yield a further 5.0 g (total 25.0 mmol, 95%) of the ditriflate; evaporation of the mother liquor gave white 1-methyl-4-aza-1-azoniabicyclo [2,2,2]octane triflate (0.5 g, 1.8 mmol, 3%) (Found: C, 34.5; H, 5.4; F, 20.3; N, 9.8%. Calc. C, 34.8; H, 5.4; F, 20.65; N, 10.1%), m.p. 214°–217° C. (dec.), with correct n.m.r. ($^1$H and $^{19}$F) parameters (see Example 1(B)).

The reaction was repeated using petroleum ether (boiling range 40°–60° C.) as the solvent (30 cm$^3$) and a deficiency of the methylating agent [1.0 g (6.1 mmol) methyl triflate, 1.4 g (12.5 mmol) 1,4-diazabicyclo-2,2,2]octane]. This gave a 75:25 molar mixture (1.6 g) of the ditriflate and monotriflate, plus unreacted 1,4-diazabicyclo[2,2,2]octane.

(D) 1-Fluoro-4-methyl-1,4-diazoniabicyclo[2,2,2]-octane Ditriflate

Using the apparatus and techniques previously employed to convert quinuclidine to N-fluoroquinuclidinium triflate in a closed reactor (R. E. Banks et al, J. Chem. Soc., Perkin Trans. I, 1988, 2805 and R. E. Banks and I. Sharif, J. Fluorine Chem., 1988, 41, 297) a degassed solution of 1-methyl-4-aza-1-azoniabicyclo[2,2,2]octane triflate (2.18 g, 7.90 mmol) and lithium triflate (1.23 g, 7.90 mmol) in cold (−35° C.), dry acetonitrile (200 cm$^3$), was treated with neat fluorine (less than 20 mmHg (2.7 kPa) pressure) until absorption of the fluorine became imperceptible (3 hours). The reaction mixture was allowed to warm to room temperature, filtered to remove lithium fluoride which had precipitated, and the filtrate rotary evaporated and recrystalized from methanol to give 1-fluoro-4-methyl-1,4-diazoniabicyclo [2,2,2]octane ditriflate (3.10 g, 6.98 mmol, 88%). (Found: C, 24.0; H, 3.6; F, 29.8; N, 6.4%. Calc. C, 24.3; H, 3.4; F, 29.95; N, 6.3%), m.p. 220°–222° C. δF (solution in D$_2$O; ext. CF$_3$CO$_2$H ref.) 1.0 (s; CF$_3$SO$_3^-$), 124.5 (br. m; FN$^+$) p.p.m., δH (same solution) 3.44 (s; CH$_3$N$^+$), 4.43 (m; 3×CH$_2$), 4.88 (m; 3×CH$_2$) p.p.m. [residual H in D$_2$O, 4.68 (s) p.p.m.].

This fluorination can also be carried out in a flow system, using a fluorine nitrogen blend (F$_2$:N$_2$ 1:9 v/v), with the same result.

EXAMPLE 2

1-Fluoro-4-methyl-1,4-diazoniabicyclo[2,2,2]octane Fluoride Tosylate

A cold (−35° C.) solution of 1-methyl-4-aza-1-azoniabicyclo [2,2,2]octane tosylate (1.44 g, 4.83 mmol) in dry acetonitrile (200 cm$^3$) was treated with neat low-pressure (less than 20 mmHg; 2.7 kPa) fluorine in a closed system, as described in Example ID, until absorption of the halogen (0.19 g, 5.00 mmol) ceased (about 2 hours). The reaction mixture was allowed to warm to room temperature then filtered to remove a white solid, which was washed with dry acetonitrile and subsequently dried in vacuo. N.m.r. analysis of this solid (0.54 g), m.p. 150° C. (dec.), indicated that it was essentially 1-fluoro-4-methyl-1,4-diazoniabicyclo-[2,2,2]octane fluoride tosylate [δF (D$_2$O soln.; ext. CF$_3$CO$_2$H ref.) −50.8 (s; F$^-$), 124.5 (br. s; FN$^+$) p.p.m., δH (same soln.) 2.36 (s; CH$_3$C$_6$H$_4$SO$_3$), 3.45 (s; CH$_3$N$^+$), 4.46 (m; 3×CH$_2$), 4.91 (m; 3×CH$_2$), 7.53 [center of an AB-system (d, 7.37; d, 7.70); C$_6$H$_4$]p.p.m. [residual H in D$_2$O, 4.76 (s) p.p.m.], although the elemental analysis was not acceptable (Found: C, 46.9; H, 5.6; F, 11.9; N, 6.3%. Calc C, 50.0; H, 6.5; F, 11.3; N, 8.3%). Recrystallization of a small sample of the solid from methanol provided impure 1-fluoro-4-methyl-1,4-diazoniabicyclo[2,2,2]octane ditosylate (Found: C, 49.3; H, 6.3; F, 5.1; N, 5.5%. Calc. C, 51.6; H, 5.9; F, 3.9; N, 5.7%), m.p. 190° C. (dec.).

Evaporation of the filtrate (from the original reaction mixture) left a yellow wax which gave a strong positive test (KI→I$_2$) for electrophilic fluorine but when analysed by n.m.r. spectroscopy in D$_2$O solution appeared to be unchanged 1-methyl-4-aza-1-azoniabicyclo-[2,2,2]octane tosylate.

Flow-fluorination (F$_2$:N$_2$ 1:9 v/v) of the tosylate (3.0 g) in cold (−40° C.) acetonitrile (100 cm$^3$) gave essentially the same result as above.

EXAMPLE 3

1-Ethyl-4-fluoro-1,4-diazoniabicyclo[2,2,2]octane Ditriflate (A) 1-Ethyl-4-aza-1-azoniabicyclo[2,2,2]octane Triflate Ethyl triflate (3.56 g, 20.0 mmol) was added dropwise to a cold (0° C.) stirred solution of 1,4-diazabicyclo[2,2,-2]octane (3.26 g, 29.1 mmol) in dry acetonitrile (25 cm$^3$) under dry nitrogen. The reaction mixture was stirred at 0° C. for 1 hour and then at 20° C. for 3 hours; no precipitate appeared. The solution was rotary evaporated at water-pump pressure, and the white solid residue remaining was washed with cold diethyl ether to remove unreacted 1,4-diazabicyclo-[2,2,2]octane and then dried in vacuo, to give 1-ethyl-4-aza-1-azoniabicyclo[2,2,2]octane triflate (5.30 g, 18.3 mmol, 91.5%) shown by $^1$H n.m.r. analysis to contain a trace of 1,4-diethyl-1,4-diazoniabicyclo[2,2,2]octane ditriflate. A pure sample of the monoquaternary salt, m.p. 117°–119° C., δH (D$_2$O soln.) 1.32 (tt; N$^+$CH$_2$CH), 3.18 (m; 3×ring CH$_2$), 3.25–3.4 (complex, two overlapping absorption systems; 3×ring CH$_2$+N$^+$CH$_2$CH$_3$), p.p.m., δF (same soln.; ext. CF$_3$CO$_2$H ref.) 0.03 (s; CF$_3$SO$_3^-$) p.p.m., was obtained by recrystallizing the slightly impure product from an ethanol-diethyl ether mixture.

(B) 1-Ethyl-4-fluoro-1,4-diazoniabicyclo[2,2,2]octane Ditriflate

The reaction described in Example 1D was repeated, using 1-ethyl-4-aza-1-azoniabicyclo[2,2,2]octane triflate (1.5 g, 5.2 mmol) in dry acetonitrile (200 cm$^3$) in place of its N-methyl analogue and an equimolar proportion of lithium triflate (0.8 g). Work-up of the product, as in Example 1D, afforded 1-ethyl-4-fluoro-1,4-diazoniabicyclo[2,2,2]octane ditriflate (1.9 g, 4.1 mmol, 80%), m.p. 236°–238° C. (dec.), δF (soln. in D$_2$O; ext. TFA) 0.02 (s; CF$_3$SO$_3$−), 124.0 (br. m; FN+) p.p.m., δH (same soln.) 1.48 (t: CH$_3$), 3.79 (q; CH$_2$CH$_3$), 4.40 (m: 3×ring CH$_2$), 4.95 (m; 3 ring CH2) p.p.m. [residual H in D$_2$O, 4.78 (s) p.p.m.].

EXAMPLE 4

1-n-Octyl-4-Fluoro-1,4-diazoniabicyclo[2,2,2]octane Ditriflate (A) 1-n-Octyl-4-aza-1-azoniabicyclo[2,2,2]octane Triflate A cold (0° C.) solution of n-octyl triflate (10.5 g, 40.0 mmol) in dry dichloromethane (50 cm$^3$) was added dropwise to a stirred, cold (0° C.), freshly-prepared solution of 1,4-diazabicyclo[2,2,2]octane (4.0 g, 36.0 mmol) in the same solvent (100 cm$^3$). The reaction mixture was stirred at 0° C. for 2 hours before being worked-up as described in Example 3A. Recrystallization (from ethanol-diethyl ether) of the crude reaction product provided 1-n-octyl-4-aza-1-diazoniabicyclo-[2,2,2]octane triflate (7.9 g, 21.1 mmol, 59%) (Found: C, 48.4; H, 8.1; N, 7.7%. Calc. C, 48.1; H, 7.75; N, 7.5%), m.p. 121°–122° C.

(B) 1-Fluoro-4-n-octyl-1,4-diazoniabicyclo[2,2,2]octane Ditriflate

The reaction described in Example 1D is repeated, using 1-n-octyl-4-aza-1-azoniabicyclo[2,2,2]octane in place of it N-methyl analogue to obtain 1-fluoro-4-n-octyl-1,4-diazoniabicyclo [2,2,2]octane ditriflate.

EXAMPLE 5

1-Fluoro-4-(2,2,2-trifluoroethyl)-1,4-diazoniabicyclo-[2,2,2]octane Ditriflate (A) 1-(2,2,2-Trifluoroethyl)-4-aza-1-azoniabicyclo-[2,2,2]octane Triflate 2,2,2-Trifluoroethyl triflate (10.0 g, 43.1 mmol) was added slowly to a stirred, freshly-prepared solution of 1,4-diazabicyclo[2,2,2]octane (7.0 g, 62.5 mmol) in dichloromethane (50 cm$^3$). The reaction mixture was stirred for 2 hours then filtered to remove a white precipitate, which was recrystallized from an ethanol-diethyl ether mixture to provide 1-(2,2,2-trifluoroethyl)-4-aza-1-azoniabicyclo [2,2,2]octane triflate (8.3 g, 24.1 mmol, 56%) (Found: C, 31.2; H, 3.8; N, 7.9%. Calc. C, 31.4; H, 4.1; N, 8.1%). m.p. 123°–125° C., δF (soln. in D$_2$O; ext. CF$_3$CO$_2$H ref.) −0.2 (s; CF$_3$SO$_3$−) 17.8 (t, $^3J_{HF}$ 9 Hz; CF$_3$CH$_2$) p.p.m., δH (same solution) 3.30 (t; 3×ring CH$_2$), 3.72 (t; 3×ring CH$_2$), 4.36 (q, $^3J_{HF}$ 9 Hz; CH$_2$CF$_3$) p.p.m.

(B) 1-Fluoro-4-(2,2,2-trifluoromethyl1,4-diazoniabicyclo[2,2,2]octane Ditriflate Using the apparatus and techniques of Example 1D, 1-(2,2,2-trifluoroethyl)-4-aza-1-azoniabicyclo[2,2,2]-octane triflate (2.0 g, 5.8 mmol) in dry acetonitrile (200 cm$^3$) also containing lithium triflate (0.9 g, 5.8 mmol) was treated with fluorine at about 10 mmHg (1.3 kPa) pressure in a closed reactor cooled to −40° C. This provided an impure sample (Found: C, 26.1; H, 2.9; F, 36.7; N, 6.9%. Calc. C, 23.4; H, 2.7; F, 37.1; N, 5.5%), m.p. 207°–210° C., of 1-fluoro-4-(2,2,2-trifluoroethyl)-1,4-diazoniabicyclo [2.2.2]octane ditriflate, δF [solution in CF$_3$CO$_2$H (also the ref.)]−2.0 (s; CF$_3$SO$_3$−), 14.0 (t, $^3J_{HF}$ 8 Hz; CF$_3$CH$_2$) 126.7 (br. s; FN+) p.p.m., δH (same soln.) 5.02 (t, $^3J_{HF}$ 8 Hz; CF$_3$CH$_2$), 5.28 (m; 3×CH$_2$), 5.50 (m; 3×CH$_2$) p.p.m.. The sample instantly liberated iodine when tested with moist starch-iodide paper; converted phenol to a mixture of o- and p-fluorophenol at room temperature; and when heated with benzene in acetonitrile-trifluoroacetic acid at 80° C. for 48 hours gave fluorobenzene.

EXAMPLE 6

Methyl-N-fluoro-N-methyl-1,4-diazoniabicyclo[2,2,2]-octane Ditriflate (A) Methyl-N-methyl-1,4-diazoniabicyclo[2,2,2]octane Triflate Methyl triflate (3.2 g, 19.5 mmol) was added dropwise to a cold (0 ° C) stirred solution of 2-methyl-1,4-diazabicyclo [2,2,2]octane (2.5 g, 20.0 mmol) in dry acetonitrile under an atmosphere of dry nitrogen. The mixture was stirred at 0° C. for 1 hour and then at 20° C. overnight. The orange solution obtained was treated dropwise with ethanol until precipitation of a white solid ceased; this solid was recovered by filtration, washed with ethanol, dried in vacuo at room temperature and shown by n.m.r. spectroscopy ($^1$H and $^{19}$F) to be 1,2,4-trimethyl-1,4-diazoniabicyclo[2,2,2]octane ditriflate (0.45 g, 0.99 mmol, 5%). Removal of acetonitrile from the filtrate in vacuo left an orange oil (3.6 g, 12.4 mmol, 64%), shown by n.m.r. spectroscopy ($^1$H and $^{19}$F) to be methyl-N-methyl-1,4-diazabicyclo [2,2,2]octane triflate.

(B) Methyl-N-fluoro-N-methyl-1,4-diazoniabicyclo-[2,2,2]octane Ditriflate

Using a Pyrex (TM) closed-system fluorination reactor, a cold (−40° C.) solution of methyl-N-methyl-1,4-diazabicyclo [2,2,2]octane triflate (3.6 g, 12.4 mmol) and lithium triflate (1.9 g, 12.2 mmol) in dry acetonitrile (200 cm$^3$) was treated with neat fluorine at 15–20 mmHg (2.0–2.7 kPa) pressure until no more was absorbed. The product solution was warmed to 20° C., filtered to remove particulate matter, and the filtrate rotary evaporated to afford a pale cream residue of methyl-N-fluoro-N-methyldiazabicyclo[2,2,2]octane ditriflate (4.9 g, 10.7 mmol, 88%) (Found: C, 26.0; H, 3.7; F, 28.6; N, 5.8%. Calc. C, 26.2; H, 3.7; F, 29.0; N, 6.1%), m.p. 146°–148° C. This residue immediately liberated iodine from aqueous potassium iodide (starch indicator) and reacted with 1-morpholinocyclohexene in dichloromethane to yield (after acidic hydrolysis) 2-fluorocyclohexanone in 86% yield.

EXAMPLE 7

Fluorinations using
1-Fluoro-4-methyl-1,4-diazoniabicyclo[2,2,2]octane
Ditriflate

(A) Anisole

A homogeneous mixture of 1-fluoro-4-methyl-1, 4-diazoniabicyclo[2,2,2]octane ditriflate (0.58 g, 1.31 mmol), anisole (0.41 g, 3.80 mmol), and dry acetonitrile was heated at 70° C. in the absence of air in a sealed Pyrex TM tube (100 cm$^3$) overnight. The product was concentrated by evaporation and the solution remaining was analysed by $^{19}$F and $^1$H n.m.r. spectroscopy. This showed that the N-fluoro salt had been converted completely to 1-methyl-4-aza-1-azoniabicyclo[2,2,2]-octane, with the formation of an about 1:1 mixture of 2- and 4-fluoroanisole. Using the triflate signal (CF$_3$SO$_3^-$) as an internal reference, the yield of the fluoroanisoles was quantitative.

(B) Phenol

A mixture of 1-fluoro-4-methyl-1,4-diazoniabicyclo [2,2,2]octane ditriflate (0.53 g, 1.19 mmol), phenol (0.33 g, 3.51 mmol), and dichloromethane (10 cm$^3$) was stirred and heated overnight at 70° C. in the absence of air in a sealed Pyrex (TM) tube (100 cm$^3$). The product was cooled to 20° C., filtered to remove the precipitate of 1-methyl-4-aza-1-azoniabicyclo[2,2,2]-octane triflate, and the filtrate concentrated by evaporation and shown by $^{19}$F n.m.r. spectroscopy to contain 2- and 4-fluorophenol in the ratio of about 3:2.

(C) 1-Morpholinocyclohexene

A mixture of 1-fluoro-4-methyl-1,4-diazoniabicyclo [2,2,2]octane ditriflate (0.38 g, 0.85 mmol) and 1-morpholinocyclohexene (0.13 g, 0.79 mmol) in dry dichloromethane (10 cm$^3$) was stirred overnight at room temperature. The product was shaken with 1M-hydrochloric acid (10 cm$^3$), and the mixture extracted with dichloromethane (4×10 cm$^3$). The extract was dried (MgSO$_4$) and rotary evaporated to remove dichloromethane. The oily residue was analysed by $^{19}$F n.m.r. spectroscopy (internal standard, C$_6$F$_6$ [5 μl]) and found to be 2-fluorocyclohexanone (yield 89%).

EXAMPLE 8

1-Chloromethyl-4-fluoro-1,4-diazoniabicyclo
[2.2.2]octane bis(tetrafluoroborate)

Sodium tetrafluoroborate (1.97 g, 17.9 mmol) in dry acetonitrile (20 cm$^3$) was run slowly into a stirred slurry of 1-chloromethyl-4-aza-1-azoniabicyclo[2,2,2]-octane chloride (3.53 g, 17.9 mmol) (a known compound, see B. Almarzogi et al., Tetrahedron, 1986, 42, 601) in the same solvent (20 cm$^3$) at ambient temperature under an atmosphere of dry nitrogen. After being stirred overnight, the reaction mixture was filtered to remove lithium chloride which had precipitated. The precipitate was washed with dry acetonitrile (20 cm$^3$) and the washings plus the filtrate were evaporated to provide slightly impure (according to n.m.r. analysis) and very pale yellow 1-chloromethyl-4-aza-1-azoniabicyclo [2.2.2]octane tetrafluoroborate (3.75 g, 15.1 mmol, 84%) [δF (solution in D$_2$O; ext. CF$_3$CO$_2$H ref.) −74.3 (s; BF$_4^-$) p.p.m., δH (same soln.) 3.29 (m; 3×CH$_2$), 3.57 (m; 3×CH$_2$), 5.11 (s; CH$_2$Cl) p.p.m. (residual H in D$_2$O, 4.75 p.p.m.)]. Recrystallisation of a small quantity of this product from an ethanol-diethyl ether mixture gave a pure white sample, m.p. 152° C., which appeared to be non-hygroscopic.

Treatment to a vigorously-stirred cold (−35° C.) solution of the slightly impure 1-chloromethyl-4-aza-1-azoniabicyclo [2.2.2]octane tetrafluoroborate (1.01 g, 7.28 mmol) and sodium tetrafluoroborate (0.80 g, 7.28 mmol) in dry acetonitrile (200 cm$^3$) with neat fluorine at 10–20 mmHg (1.3–2.7 kPa) pressure until its uptake appeared to cease provided 1-chloromethyl-4-fluoro-1,4-diazoniabicyclo [2.2.2]octane bis(tetrafluoroborate) (2.20 g, 6.51 mmol, 89%), almost pure according to elemental analysis (C, 24.4: H, 4.6: N, 7.9%. Calc. C, 23.7; H, 3.95; N, 7.9%) and n.m.r. analysis [δF (solution in D$_2$O; ext. CF$_3$CO$_2$H ref.) 125.5 (br. s; FN$^+$), −72.0 (s; BF$_4^-$) p.p.m. (a trace of F$^-$ impurity caused an absorption at −50.7 p.p.m.); δH (same soln.) 4.53 (m; 3×CH$_2$), 4.97 (m; 3×CH$_2$), 5.50 (s; CH$_2$Cl) p.p.m. (residual H in D$_2$O, 4.70 p.p.m.)](isolated by filtering the product to remove NaF then evaporating the filtrate to remove CH$_3$CN). This bis(tetrafluoroborate) melted with decomposition at 170° C. (turning brown at about 160° C.) after recrystallisation from an acetonitrile-diethyl ether mixture; rapidly liberated iodine from potassium iodine (moist starch-iodide paper); and converted phenol in warm acetonitrile to a mixture of ortho- and parafluorophenol.

EXAMPLE 9

1-Chloromethyl-4-fluoro-1,4-diazoniabicyclo[2.2.2]-
octane Ditriflate

A solution of lithium triflate (3.81 g, 24.4 mmol) in dry acetonitrile (20 cm$^3$) was added to a stirred slurry of 1-chloromethyl-4-aza-1-azoniabicyclo[2,2,2]-octane chloride (4.81 g, 24.4 mmol) in the same solvent (25 cm$^3$) at ambient temperature under dry nitrogen. After being stirred overnight, the reaction mixture was filtered to remove lithium chloride, and the latter was washed with dry acetonitrile (20 cm$^3$). Evaporation of the washings and the filtrate left a yellowish white solid which was recrystallised from an ethanol-diethyl ether mixture to provide white 1-chloromethyl-4-aza-1-azoniabicyclo [2,2,2]octane triflate (6.68 g, 21.5 mmol, 88%), m.p. 152° C. (dec.; charring commenced at 130° C.), δF (solution in D$_2$O; ext. CF$_3$CO$_2$H ref.) 0.1 (s; CF$_3$SO$_3^-$) p.p.m., δH (same soln.) 3.29 (m; 3×CH$_2$), 3.57 (m; 3×CH$_2$), 5.12 (s; CH$_2$Cl) ppm (residual H in D$_2$O, 4.75 p.p.m.).

Treatment of a cold (−35° C.) solution of 1-chloromethyl-4-aza-1-azoniabicyclo[2.2.2]octane triflate (3.20 g, 10.3 mmol) and lithium triflate (2.55 g, 16.3 mmol) in dry acetonitrile (200 cm$^3$) with neat fluorine at low pressure (10–20 mmHg; 1.3–2.7 kPa) until absorption appeared to cease provided (after the usual work-up procedure to remove lithium fluoride and acetonitrile as described above) 1-chloromethyl-4-fluoro-1,4-diazoniabicyclo [2.2.2]octane ditriflate (4.77 g, 10.0 mmol, 97%) (Found C, 22.2; H, 3.1; N, 5.5%. Calc. C, 22.6; H, 2.9; N, 5.85%), m.p. 165° C. (after recrystallisation from methanol-diethyl ether), δF (solution in D$_2$O; ext. CF$_3$CO$_2$H ref.) 125.2 (br.m; FN$^+$), 0.0 (s; CF$_3$SO$_3^-$) p.p.m., δH (same soln.) 4.65 (m; 3×CH$_2$), 5.10 (m; 3×CH$_2$), 5.61 (s; CH$_2$Cl) p.p.m.. The product immediately oxidizes iodide ion to iodine at room temperature (test with moistened starch-iodide paper) and will act as a positive fluorinating agent towards appropriate electron-rich carbon species, eg. 1-morpholinocyclohexene and phenol.

I claim:

1. An N-fluorinated diazabicycloalkane compound having the following Formula I:

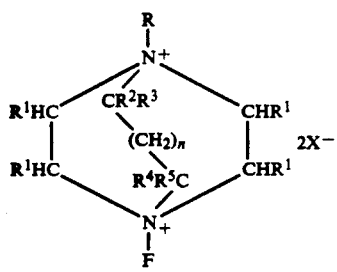

wherein n represents 0, 1, or 2; R represents a quaternizing organic group selected from the group consisting of aliphatic unsubstituted linear or branched $C_1$–$C_{16}$ alkyl groups, benzyl, benzyl substituted by one to three $C_1$–$C_4$ alkyl groups, $C_1$–$C_{10}$ perfluoroalkyl groups, $C_1$–$C_{16}$ partially halogenated alkyl groups, and 3-(4-fluoro-1,4-diazoniabicyclo(2,2,2)oct-1-yl)propyl; each $R^1$, $R^2$, $R^3$, $R^4$ and $R^5$ independently is selected from the group consisting of hydrogen, $C_1$–$C_6$ alkyl, aryl, $C_1$–$C_6$ alkyl-substituted aryl or aryl-substituted $C_1$–$C_6$ alkyl and each $X^-$ independently is a counterion or $2X^-$ represents a single divalent counterion, either of which are capable of forming a strable salt with the dication portion of the compound.

2. An N-fluorinated diazabicycloalkane derivative in accordance with claim 1 wherein said compound is 1-chloromethyl-4-fluoro-1,4-diazoniabicyclo[2,2,2]octane ditriflate.

3. The compound according to claim 1, wherein each $R^1$ independently is selected from the group consisting of hydrogen, methyl, benzyl and phenyl.

4. The compound according to claim 3, wherein each $R^1$ is hydrogen.

5. The compound according to claim 1, wherein each of $R^2$ to $R^5$ independently is selected from the group consisting of hydrogen, methyl, benzyl and phenyl.

6. The compound according to claim 5, wherein each of $R^2$ to $R^5$ is hydrogen.

7. The compound according to claim 1, wherein each $X^-$ independently is selected from the group consisting of fluoride; fluorosulfate; methanesulfonate; methyl sulfate; triflate; nonaflate; tosylate; tetrafluoroborate; tetraphenylborate; hexafluorophosphate; chlorate, or hexafluoroantimonate or $2X^-$ is sulfate.

8. The compound according to claim 7, wherein one $X^-$ is selected from the group consisting of tosylate or triflate and the other $X^-$ is triflate.

9. The compound according to claim 1, wherein n is 0 and each $R_1$ is hydrogen.

10. An N-fluorinated diazabicycloalkane compound having the following Formula I:

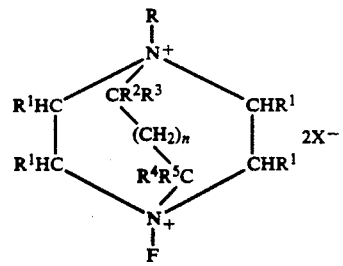

wherein n is 0, 1 or 2; R is a quaternizing organic group selected from the group consisting of aliphatic unsubstituted linear or branched $C_1$–$C_{16}$ alkyl groups, benzyl, benzyl substituted by one to three $C_1$–$C_4$ alkyl groups, $C_1$–$C_{10}$ perfluoroalkyl groups, $C_1$–$C_{16}$ partially fluorinated alkyl groups, and 3-(4-fluoro-1,4-diazoniabicyclo[2,2,2]oct-1-yl)-propyl; each $R^1$, $R^2$, $R^3$, $R^4$ and $R^5$ independently are selected from the group consisting of hydrogen, methyl, benzyl and phenyl; and each $X^-$ independently is selected from the group consisting of fluoride, fluorosulfate, methanesulfonate, methyl sulfate, triflate, nonaflate, tosylate, tetrafluoroborate, hexafluorophosphate, chlorate, and hexafluoroantimonate; or $2X^-$ is sulfate.

11. An N-fluorinated 1,4-diazabicyclo[2,2,2]octane compound having the following Formula IA:

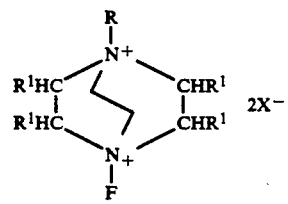

wherein R is a quaternizing organic group selected from the group consisting of $C_1$–$C_8$ alkyl groups, benzyl, benzyl substituted by one to three $C_1$–$C_4$ alkyl groups, $C_1$–$C_8$ perfluoroalkyl groups, $C_1$–$C_8$ fluorinated alkyl groups, and 3-(4-fluoro-1,4-diazoniabicyclo [2,2,2]oct-1-yl)propyl; each $R^1$, $R^2$, $R^3$, $R^4$ and $R^5$ independently are selected from the group consisting of hydrogen, methyl and phenyl; and each $X^-$ is selected from the group consisting of fluoride, triflate and tosylate.

12. An N-fluorinated 1,4-diazabicyclo[2,2,2]octane compound having the following Formula II:

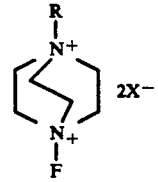

wherein R is a quaternizing organic group selected from the group consisting of $C_1$–$C_8$ alkyl groups, benzyl, benzyl substituted by one to three $C_1$–$C_4$ alkyl groups, $C_1$–$C_8$ perfluoroalkyl groups, $C_1$–$C_8$ partially fluorinated alkyl groups, and 3-(4-fluoro-1,4-diazoniabicyclo [2,2,2]oct-1-yl)propyl; and each $X^-$ independently is selected from the group consisting of fluoride, triflate and tosylate.

13. An N-fluorinated diazabicycloalkane derivative in accordance with claim 1 wherein said compound is 1-fluoro-4-methyl-1,4-diazoniabicyclo[2,2,2]octane ditriflate.

14. An N-fluorinated diazabicycloalkane derivative in accordance with claim 1 wherein said compound is 1-fluoro-4-methyl-1,4-diazoniabicyclo[2,2,2]octane fluoride tosylate.

15. An N-fluorinated diazabicycloalkane derivative in accordance with claim 1 wherein said compound is 1-ethyl-4-fluoro-1,4-diazoniabicyclo[2,2,2]octane ditriflate.

16. An N-fluorinated diazabicycloalkane derivative in accordance with claim 1 wherein said compound is 1-fluoro-4-n-octyl-1,4-diazoniabicyclo[2,2,2]octane ditriflate.

17. An N-fluorinated diazabicycloalkane derivative in accordance with claim 1 wherein said compound is 1-fluoro-4-(2,2,2-trifluoroethyl)-1,4-diazoniabicyclo[2,2,2]octane ditriflate.

18. An N-fluorinated diazabicycloalkane derivative in accordance with claim 1 wherein said compound is methyl-N-fluoro-N-methyl-1,4-diazoniabicyclo[2,2,2]octane ditriflate.

19. An N-fluorinated diazabicycloalkane derivative in accordance with claim 1 wherein said compound is 1-chloromethyl-4-fluoro-1,4-diazoniabicyclo[2,2,2]octane bis(tetrafluoroborate).

* * * * *